United States Patent [19]
Hely

[11] Patent Number: 6,142,966
[45] Date of Patent: Nov. 7, 2000

[54] WRIST ORTHOSIS

[75] Inventor: John P. Hely, Oxnard, Calif.

[73] Assignee: Weber Orthopedic, Inc., Santa Paula, Calif.

[21] Appl. No.: 09/368,941

[22] Filed: Aug. 5, 1999

[51] Int. Cl.[7] .............................. A61F 5/00; A61F 13/00; A61F 5/37
[52] U.S. Cl. .................. 602/64; 602/5; 602/20; 602/21; 602/60; 128/879
[58] Field of Search .................. 602/5, 20, 21, 602/60, 62, 63, 64; 2/16, 159, 160, 161.1, 161.2, 161.3, 161.4, 161.5, 161.6, 161.7, 161.8; D24/190; 473/60, 61, 62; 128/878, 879

[56] References Cited

U.S. PATENT DOCUMENTS

| D. 242,172 | 11/1976 | Borenstein | 602/64 X |
|---|---|---|---|
| 3,238,939 | 3/1966 | Stubbs | 602/64 |
| 3,256,882 | 6/1966 | Huber | 602/64 |
| 3,512,776 | 5/1970 | Thomas, Sr. | 602/64 |
| 3,533,407 | 10/1970 | Smith | 602/64 |
| 5,014,689 | 5/1991 | Meunchen et al. | 602/64 |
| 5,513,657 | 5/1996 | Nelson | 128/879 |

OTHER PUBLICATIONS

Pp. 29, 30, 31 & 32, cover page, and inside cover page of MiAnna Orthopedic Inc., brochure, entitled "Orthopedic Catalog". Copyright 1993.

EZY WRAP brochure entitled The #1 Member of our Wrist Support Family, Copyright 1992.

Medical Specialties Inc. brochure entitled "Specialized Wrist Supports", Copyright 1994.

*Primary Examiner*—Kim M. Lee
*Attorney, Agent, or Firm*—William W. Haefliger

[57] ABSTRACT

A brace for the wrist of a human hand, comprising in combination, an elongated, flexible, relatively thin sheet having an inner side to receive the underside of the user's wrist, the sheet having first and second flaps to wrap over outer side portions of the user's wrist to envelop the wrist, the sheet consisting of elastomer which is foamed and which is bi-directionally stretchable, a first strap at the inner side of the sheet and locally anchored to the sheet to independently wrap adjacent a portion of the user's wrist and then over a portion of one of the flaps, primary retention elements releasably attach the first strap to said one of the flaps, thereby to initially hold the sheet to the wrist, secondary retention elements to releasably attach the flaps together when the flaps are wrapped at about the wrist to envelop the wrist, and to tension said flaps, thereby secondarily holding the sheet to the wrist and to brace the wrist, whereby dual tensioning of the brace is provided, and a hole through the sheet at a location between the flaps, to receive the thumb of the human hand.

15 Claims, 3 Drawing Sheets

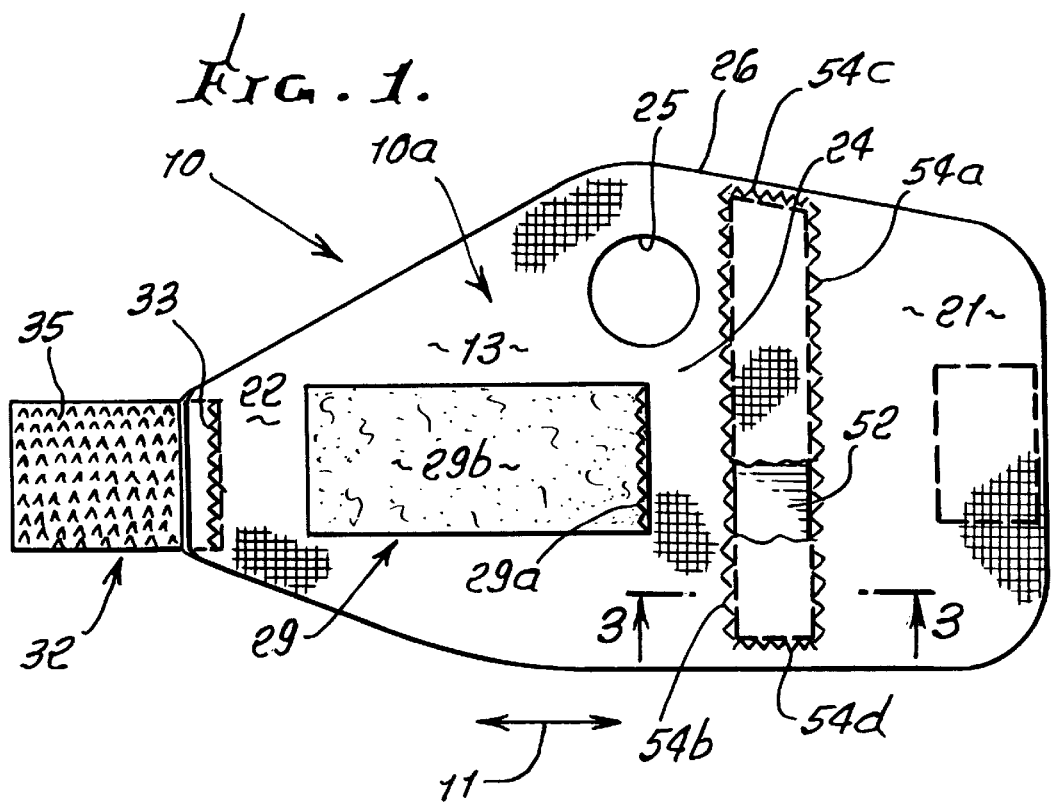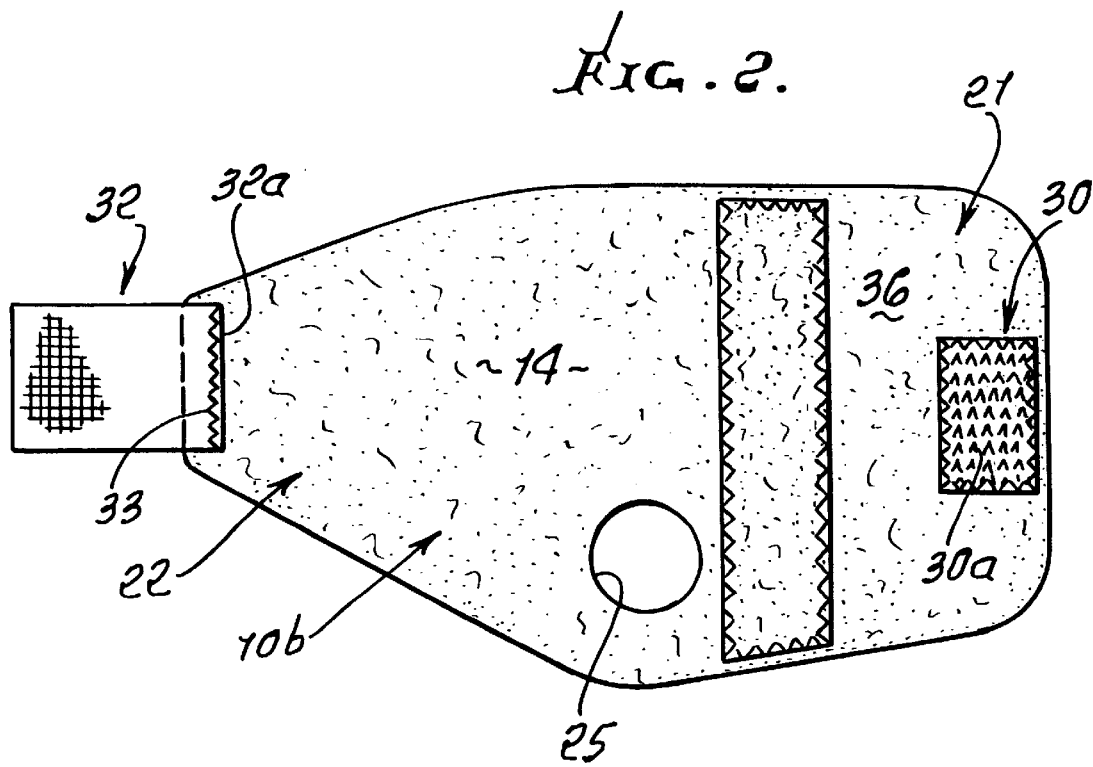

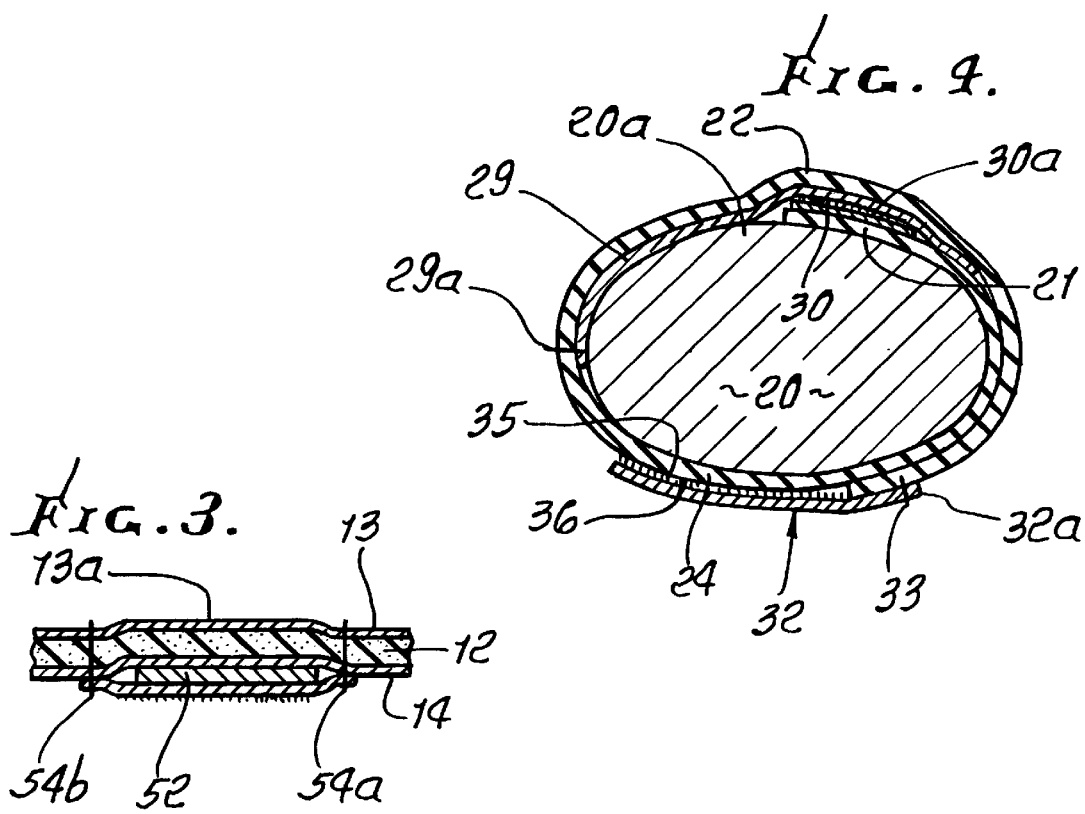
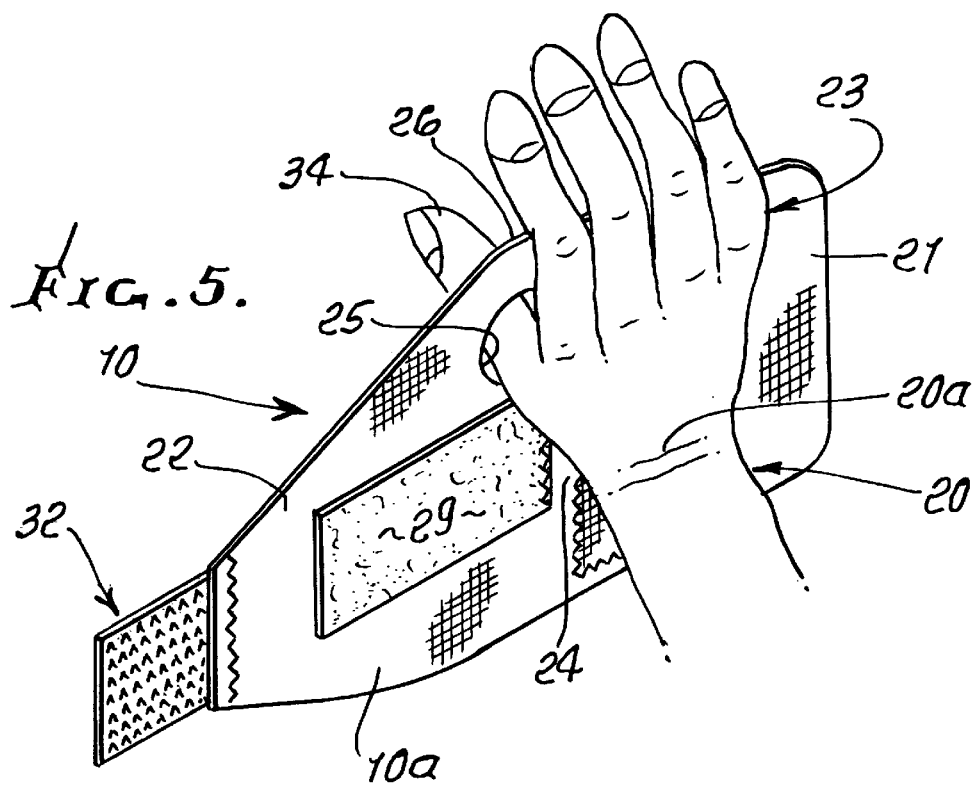

WRIST ORTHOSIS

BACKGROUND OF THE INVENTION

This invention relates generally to wrist braces, and more particularly to an improved, simple, stretchable, wrist brace in the form of a wrap easily attached to one wrist while the user manipulates the wrap with his or her other hand.

There is continual need for simple, effective wrist orthoses which incorporate advantages as are embodied in the presently disclosed brace.

SUMMARY OF THE INVENTION

It is a major object of the invention to provide an improved wrist brace meeting the above needs. Basically, the brace comprises:

a) an elongated, flexible relatively thin sheet having an inner side to receive the underside of the user's wrist, the sheet having first and second flaps to wrap over outer side portions of the user's wrist to envelop the wrist, b) the sheet consisting of elastomer which is foamed and which is bi-directionally stretchable, c) a first strap at the inner side of the sheet and locally anchored to the sheet to independently wrap adjacent a portion of the user's wrist and then over a portion of one of the flaps, d) primary retention elements releasably to attach the first strap to the one of the flaps, thereby to initially hold the sheet to the wrist, e) secondary retention elements to releasably attach the flaps together when the flaps are wrapped about the wrist to envelop the wrist, and to tension the flaps, thereby secondarily holding the sheet to the wrist and to brace the wrist, whereby dual tensioning of the brace is provided, f) and a hole through the sheet at a location between the flaps, to receive the thumb of the human hand.

Another object is to provide a flexible holder, as in the form of a secondary strap, attached to the second flap to provide for secondarily holding together of the two flaps in spaced relation to the hole, as in adjustably tensioned condition. Typically, the secondary strap extends from the end of the second flap back over the outer side of the first flap, to which the holder is adjustably attachable as by a hook and pile connection. In this regard, the first strap may also have hook and pile connection to the first flap, with adjustable tensioning provided. Accordingly, the two straps independently afford adjustably tensioning of the two flaps of the brace as applied to the wrist of the wearer, whereby a positive, dual adjustable, and comfortable bracing effect is created.

An additional object is provision of a brace stiffener carried by the sheet intermediate the two flaps. That stiffener is typically elongated, and concave, along its length facing toward the inner side of the brace, to conform to the palm of the user's hand, when the wrap is tensioned, as referred to.

These and other objects and advantages of the invention, as well as the details of an illustrative embodiment, will be more fully understood from the following specification and drawings, in which:

DRAWING DESCRIPTION

FIG. 1 is a plan view of the inner side of a wrist brace, extended in flat condition;

FIG. 2 is a plan view of the opposite or outer side of the FIG. 1 wrist brace;

FIG. 3 is a section taken in elevation on lines 3—3 of FIG. 1;

FIG. 4 is a section taken on lines 4—4 of FIG. 7, through the brace wrapped and tightened about the wrist of a user; and FIGS. 5–7 are perspective views showing steps in application of the brace to the wrist of a user.

DETAILED DESCRIPTION

Figure 6:
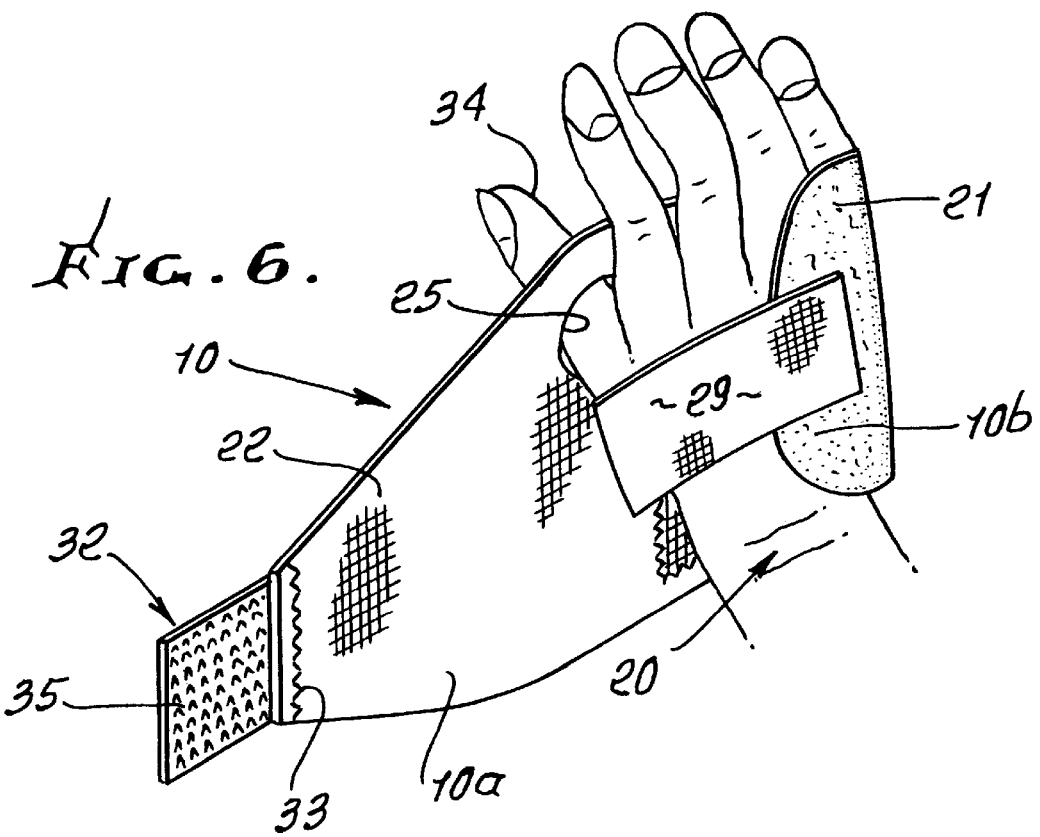

FIGS. 1 and 2 show inner and outer sides 10a and 10b of a brace wrap sheet 10 which is elongated in longitudinal direction 11, and flexible. The sheet may advantageously include a base pad layer 12 of an elastomer such as foamed rubber (NEOPRENE being an example) of a thickness between about ⅟32 inch and ¼ inch. The sheet may comprise a composite, which includes a thin flexible layer 13 adherent to one side of the base layer 12, to define the inner side 10a, and an outer thin flexible layer 14 adherent to the opposite side of base layer 12, as is clear from FIG. 3. Layer 13 may be formed from the commercial elastomer product known as STARSKIN, 3 mm #1 smooth skin plush royal 403, produced by St. Albans Rubber Ltd., St. Albans, Herts, England. Layer 14 may be formed from the same elastomer as layer 13, or a similar elastomer, and its thickness may be about 3 mm, for example. Such construction enables great versatility or adjustability of the brace wrap sheet 10, which may advantageously be bi-directionally resiliently stretchable to enable exertion of a wide range of compressive forces on the wrist 20 of a wearer, in the wrapped or applied condition, as seen in FIG. 7.

Figure 7:
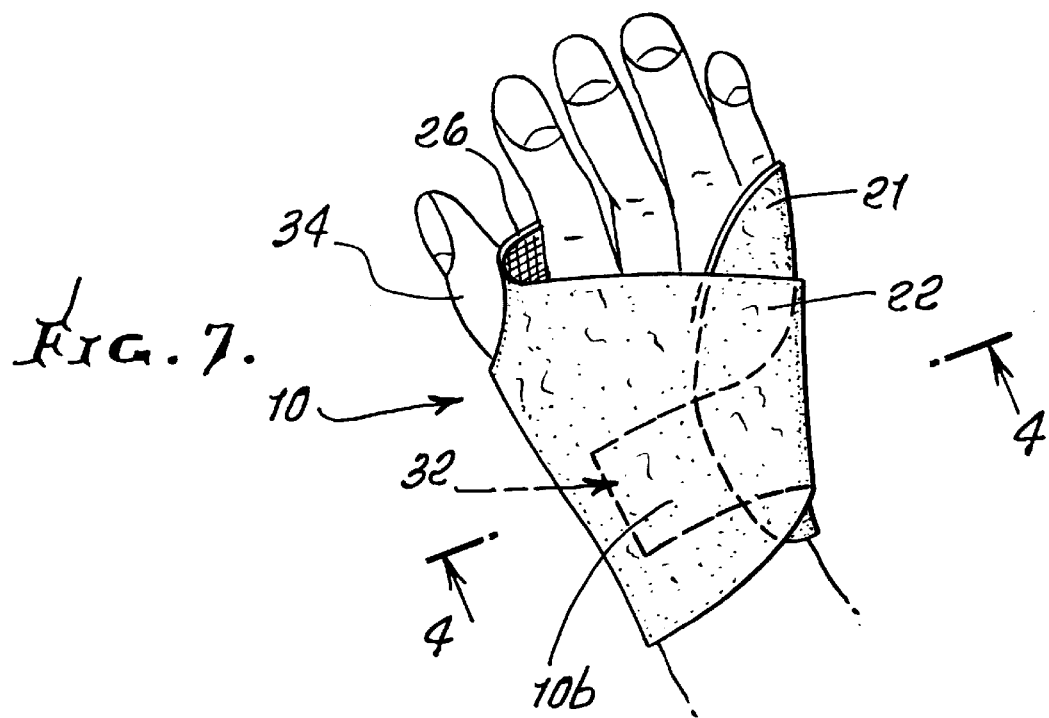

The wrap sheet 10 includes first and second flaps 21 and 22 to wrap over the outer side portion 20a or portions, of the user's wrist 20, as depicted in FIGS. 5–7; this takes place after the user's hand 23 is placed palm side down on the inner side 10a of the wrap sheet, at the mid-portion 24 thereof between endwise spaced flaps 21 and 22. See FIGS. 1 and 4, and also FIG. 5, showing wrap mid-portion 24 receiving placement of the underside (palm side) of the user's wrist. A thumb hole 25 is preferably provided through the mid-portion 24, near one edge 26 of the wrap, to locate wrist placement, intermediate flaps 21 and 22, as seen in FIG. 5, and also to facilitate efficient and comfortable wrapping, as seen in FIGS. 4–7.

A first strap 29 is provided at the inner side of the wrap sheet 10, and locally anchored to 10, as at strap end location 29a. Strap 29 can therefore independently fold, endwise of the sheet, for example clockwise, to overlap the end portion of flap 21, previously folded counterclockwise about the wrist, as seen in FIG. 4. See also FIG. 6. Strap 29 is longitudinally endwise stretchable in direction 11, seen in FIG. 1, whereby it can be easily pulled to elongate and then releasably connect onto folded flap 21, to form a tensioning loop (as defined by 29 and 21 in FIG. 4 mode) gripping the wrist independently of wrappers of flap 22. See in this regard the hook and loop connection formed at and by the surface 29b of the strap 29, and by the surface 30a of patch 30 connected to flap 21 as seen in FIG. 2. The strap 29, the wrap sheet intermediate portion 24, and flap 21 are resiliently and stretchably tensioned at this time, and may be regarded as primary retention elements. See FIG. 6.

Also provided are secondary retention elements to releasably attach the flaps 21 and 22 when both flaps are wrapped about the wrist to envelop the wrist, and to tension those flaps, as seen in FIG. 7, thereby secondarily holding the sheet compressively to the wrist and bracing the wrist, whereby dual tensioning by the brace is provided. In the example, a flexible holder is provided, as in the form of a short secondary strap 32, locally anchored to 10, as at strap end 32a. Note stitching 33 anchoring end 32a to the narrowed end of flap 22 (which tapers toward 32a), and in alignment with strap 29, as seen in FIG. 1. As seen in FIGS. 4 and 7, the secondary strap 32 wraps clockwise about flap 21, after flap 22 is folded clockwise up and back over the wrist, and over the end extent of flap 21. The wrist is anchored or held in FIG. 5 position during such folding of 22, and of strap 32, into FIG. 7 position, by the interfitting of thumb 34 in thumb hole 25, whereby ease of application of the brace to the wrist is enabled, and continued during stretching of flap 22 and strap 32, whereby thumb hole 25 has multiple functions in relation to the various elements of the brace.

Secondary retention of strap 32 to the outer side of flap 21 is for example provided by hook and pile elements, such as locally at 35 at the surface of the flap 32, and widely at 36 at the extensive outer surface of flap 21. A large interattachment surface is provided, enabling strap 32 to attach to 21 in any of a large number or ranges of position, best suited for adjustable and most comfortable bracing of the wrist, or wrists of different sizes and shapes.

FIGS. 1 and 3 show the preferable, but optional, provision of a rigid, laterally extending wrap 10, as at its inner side, as by fabric patch 52a.

For this purpose, thin layer 13 covers the stiffener 52 at 13a, and stitching attaches layer 13a close to edges of the stiffener, as at 54a - - - 54d. The stiffener is preferably slightly curved, to be lengthwise concave toward the user's palm, proximate finger joints, for best wrist and hand support, when the wrap 10 is tensioned as in FIG. 7.

The none wrap as described constitutes the preferred mode or form of the invention; however, there are a large number of other usable modes, within the scope of the elements of the following claims.

I claim:

1. A wrist brace comprising in combination,
   a) an elongated, flexible, relatively thin sheet having an inner side adapted to receive the underside of the user's wrist, said sheet having first and second flaps, said flaps having inner and outer surfaces and are adapted to wrap over outer side portions of the user's wrist to envelop the wrist,
   b) said sheet consisting of an elastomer which is foamed and which is bi-directionally stretchable,
   c) a first strap positioned on the inner side of the sheet, having a first end locally anchored to said sheet and a second free end, said first strap adapted to independently wrap adjacent a portion of the user's wrist and then over the outer surface of one of the flaps to be secured thereto,
   d) primary retention elements to releasably attach the first strap to said one of the flaps, thereby to initially hold the sheet to the wrist,
   e) secondary retention elements to releaseably attach the flaps together when the flaps are wrapped about the wrist to envelop the wrist, and to tension said flaps, thereby secondarily holding the sheet to the wrist, whereby dual tensioning of the brace is provided,
   f) and a hole through the sheet at a location between the flaps, to receive the thumb of the hand.

2. The combination of claim 1 wherein said primary retention elements comprise hook and pile elements.

3. The combination of claim 1 wherein said secondary retention elements comprise hook and pile elements.

4. The combination of claim 3 including a flexible holder attached to said second flap and carrying one of the secondary hook and pile elements.

5. The combination of claim 4 wherein said flexible holder comprises a secondary strap, said second flap edgewise tapering lengthwise toward said second strap.

6. The combination of claim 5 wherein said first strap has connection to the sheet proximate said hole.

7. The combination of claim 6 including a stiffener carried by said sheet intermediate said flaps, said connection is laterally offset from said hole, and said stiffener extending in a lateral direction and proximate to said hole and connection.

8. The combination of claim 1 wherein said hole through the sheet is at a location laterally offset from the first strap to receive the thumb of said human hand.

9. The combination of claim 1 including a stiffener carried by said sheet intermediate said flaps.

10. The combination of claim 9 wherein said stiffener is elongated and concave along its length toward the inner side of the brace, to conform to the palm of the user's hand.

11. A brace for the wrist of a human hand, comprising in combination,
    a) an elongated, flexible, relatively thin sheet having an inner side adapted to receive the underside of the user's wrist, said sheet having first and second flaps, said flaps having inner and outer surfaces and are adapted to wrap over portions of the user's wrist to envelop the wrist,
    b) said sheet consisting of a n elastomer which is foamed and which is bi-directionally stretchable,
    c) a first strap positioned on the inner side of the sheet, having a first end locally anchored to said sheet and a second free end, said first strap adapted to independently wrap adjacent a portion of the user's wrist and then over the outer surface of one of the flaps to be secured thereto,
    d) primary retention elements to releasably attach the first strap to one of the flaps, thereby to initially position the sheet adjacent the wrist,
    e) secondary retention elements to releaseably retain the flaps in superimposed relation when the flaps are wrapped at the wrist, and to tension at least one of said flaps, thereby holding the sheet to the wrist and to brace the wrist,
    f) and a thumb hole defined by the sheet at a location proximate at least one of the flaps, to receive the thumb of the hand.

12. The combination of claim 11 wherein said primary retention elements comprise hook and pile elements.

13. The combination of claim 11 wherein said secondary retention elements comprise hook and pile elements.

14. The combination of claim 13 wherein one of said secondary retention elements is at the outer side of the first flap, which is elongated.

15. The combination of claim 14 wherein the other of said secondary retention elements is at an end of the elongated first flap.

* * * * *